(12) United States Patent
Grant et al.

(10) Patent No.: US 9,120,800 B2
(45) Date of Patent: Sep. 1, 2015

(54) PROCESS FOR THE PREPARATION OF OXYMORPHONE ALKALOID AND OXYMORPHONE SALTS

(71) Applicant: JOHNSON MATTHEY PUBLIC LIMITED COMPANY, London (GB)

(72) Inventors: Ewart Grant, Devens, MA (US); Brian Heinrich, Devens, MA (US); Saroop Matharu, Devens, MA (US); Nicolas Archer, Edinburgh (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 14/173,314

(22) Filed: Feb. 5, 2014

(65) Prior Publication Data

US 2015/0038715 A1    Feb. 5, 2015

Related U.S. Application Data

(60) Provisional application No. 61/861,777, filed on Aug. 2, 2013.

(51) Int. Cl.
*C07D 489/08* (2006.01)
*C07D 489/02* (2006.01)

(52) U.S. Cl.
CPC ............ *C07D 489/02* (2013.01); *C07D 489/08* (2013.01)

(58) Field of Classification Search
USPC ...................................... 546/45, 44; 514/282
See application file for complete search history.

(56) References Cited

U.S. PATENT DOCUMENTS

| | | |
|---|---|---|
| 3,332,950 A | 7/1967 | Blumberg et al. |
| 3,433,791 A | 3/1969 | Bentley |
| 3,812,132 A | 5/1974 | Grew et al. |
| 3,845,770 A | 11/1974 | Theeuwes et al. |
| 3,916,899 A | 11/1975 | Theeuwes et al. |
| 4,063,064 A | 12/1977 | Saunders |
| 4,088,864 A | 5/1978 | Theeuwes |
| 4,200,098 A | 4/1980 | Ayer |
| 4,285,987 A | 8/1981 | Ayer |
| 4,861,598 A | 8/1989 | Oshlack |
| 4,957,681 A | 9/1990 | Klimesch |
| 5,071,985 A | 12/1991 | Andre |
| 5,215,758 A | 6/1993 | Krishnamurthy |
| 5,273,760 A | 12/1993 | Oshlack |
| 5,286,493 A | 2/1994 | Oshlack |
| 5,324,351 A | 6/1994 | Oshlack |
| 5,356,467 A | 10/1994 | Oshlack |
| 5,472,712 A | 12/1995 | Oshlack |
| 5,869,669 A | 2/1999 | Huang |
| 5,922,876 A | 7/1999 | Huang |
| 5,948,788 A | 9/1999 | Huang |
| 5,952,495 A | 9/1999 | Huang |
| 5,981,751 A | 11/1999 | Mudryk |
| 6,008,354 A | 12/1999 | Huang |
| 6,008,355 A | 12/1999 | Huang |
| 6,013,796 A | 1/2000 | Huang |
| 6,177,567 B1 | 1/2001 | Chiu |
| 6,262,266 B1 | 7/2001 | Chiu |
| 6,291,675 B1 | 9/2001 | Coop |
| 6,365,742 B1 | 4/2002 | Mudryk |
| 6,395,900 B1 | 5/2002 | Coop |
| 6,403,798 B2 | 6/2002 | Chiu |
| 6,723,894 B2 | 4/2004 | Fist |
| 6,864,370 B1 | 3/2005 | Lin |
| 6,949,645 B1 | 9/2005 | Francis |
| 7,071,336 B2 | 7/2006 | Francis |
| 7,129,248 B2 | 10/2006 | Chapman |
| 7,153,966 B2 | 12/2006 | Casner |
| 7,851,482 B2 | 12/2010 | Dung |
| 8,134,002 B2 | 3/2012 | Huang |
| 8,217,175 B2 * | 7/2012 | Wang et al. ..................... 546/45 |
| 2002/0045755 A1 | 4/2002 | Coop |
| 2003/0129230 A1 | 7/2003 | Baichwal |
| 2003/0129234 A1 | 7/2003 | Baichwal |
| 2003/0157167 A1 | 8/2003 | Kao |
| 2006/0009479 A1 | 1/2006 | Bailey |
| 2006/0173029 A1 | 8/2006 | Chapman |
| 2008/0045716 A1 | 2/2008 | Smith |
| 2008/0125592 A1 | 5/2008 | Huang |
| 2008/0312442 A1 | 12/2008 | Buehler |
| 2010/0274019 A1 | 10/2010 | Huang |
| 2013/0102784 A1 | 4/2013 | Reisch |

FOREIGN PATENT DOCUMENTS

| | | |
|---|---|---|
| EP | 0359647 | 3/1990 |
| EP | 2377866 | 10/2011 |
| WO | 9902529 | 1/1999 |
| WO | 0129048 | 4/2001 |
| WO | 2005028483 | 3/2005 |
| WO | 2005097801 | 10/2005 |
| WO | 2007103105 | 9/2007 |
| WO | 2008072018 | 6/2008 |

(Continued)

OTHER PUBLICATIONS

Andrew Coop et al., "L-Selectride as a General Reagent for the O-Demethylation and N Decarbomethoxylation of Opium Alkaloids and Derivatives," J. Org. Chem., 1998, 63 (13), pp. 4392-4396.

(Continued)

*Primary Examiner* — Charanjit Aulakh (57) ABSTRACT

The present invention provides a process for preparing an oxymorphone acid adduct, said process comprising hydrogenating an aqueous solution of 14-hydroxymorphinone and an acid to form a solution of the oxymorphone acid adduct, wherein the hydrogenation is carried out at one or more temperatures greater than 40° C. in the presence of a hydrogenation catalyst and hydrogen gas, wherein the level of 6α-oxymorphol produced is ≤3.00 area % as determined by HPLC.

20 Claims, 3 Drawing Sheets

(56) References Cited

FOREIGN PATENT DOCUMENTS

| | | |
|---|---|---|
| WO | 2008118654 | 10/2008 |
| WO | 2013188418 | 12/2013 |
| WO | 2014013313 | 1/2014 |

OTHER PUBLICATIONS

Ulrich Weiss, Derivatives of Morphine. II. Demethylation of 14-hydroxycodeinone. 14 Hydroxymorphinone and 8,14-Dihydroxydihydromorphinone, J. Org. Chem., 1957, 22 (11), pp. 1505-1508.

Marton et al., "Herstellung von 6, 14-Ethenomorphinan-Derivaten," Monatshefte für Chemie, vol. 125, pp. 1229-1239 (1994).

Hosztafi et al., "Reactions of Azodicarboxylic Esters with Amines," Scientia Pharmaceutica, vol. 55, pp. 61-75 (1987).

Andre et al., "O-Demethylation of Opioid Derivatives with Methane Sulfonic Acid / Methionine: Application to the Synthesis of Naloxone and Analogues," Synthetic Communications, vol. 22, No. 16, pp. 2313-2327 (1992).

Bari et al., "Impurity profile: Significance in Active Pharmaceutical Ingredient," Eurasian Journal of Analytical Chemistry, vol. 2, No. 1, 2007, pp. 32-53.

International Search Report and Written Opinion of PCT/GB2014/050317 mailed Apr. 6, 2014.

Scammels et al., Improved synthesis of 14-hydroxy opioid pharmaceuticals and intermediates; RSC Advances, 2012, 2, 113818-11325.

* cited by examiner

PROCESS FOR THE PREPARATION OF OXYMORPHONE ALKALOID AND OXYMORPHONE SALTS

FIELD OF THE INVENTION

The present invention concerns an improved process for the synthesis of oxymorphone alkaloid and oxymorphone salts, such as the hydrochloride, having improved impurity profiles.

SUMMARY OF THE INVENTION

We have developed an improved process which overcomes the disadvantages associated with the prior art methods. The present process is suitable for large-scale manufacture of oxymorphone alkaloid and oxymorphone salts.

DETAILED DESCRIPTION OF THE INVENTION

In one aspect, therefore, the invention provides a process for preparing an oxymorphone acid adduct, said process comprising hydrogenating an aqueous solution of 14-hydroxymorphinone and an acid to form a solution of the oxymorphone acid adduct, wherein the hydrogenation is carried out at one or more temperatures greater than 40° C. in the presence of a hydrogenation catalyst and hydrogen gas, wherein the solution of oxymorphone acid adduct comprises 6α-oxymorphol in an amount 3.00 area % as determined by HPLC.

The process comprises hydrogenating an aqueous solution of 14-hydroxymorphinone and an acid. The pH of the initial reaction mixture may be any suitable pH which does not adversely affect the impurity profile of the oxymorphone adduct solution produced. In one embodiment, the pH of the reaction mixture may be in the range of about ≥1.0 to about <7.0. In some embodiments, the pH may be ≥about 1.5. In some embodiments, the pH may be ≥about 2.0. In some embodiments, the pH may be ≤about 6.5. In some embodiments, the pH may be ≤about 6.0. In one embodiment, the pH of the reaction mixture may be in the range of about ≥2.0 to about ≤about 5.5. The pH may increase during the course of the reaction and, if desired, the pH may be adjusted as appropriate to lower the pH through the addition of further acid or a solution of acid/water.

The acid may be selected from the group consisting of acetic acid, phosphoric acid, citric acid, tartaric acid, oxalic acid, hydrochloric acid and hydrobromic acid. In one embodiment, the acid is acetic acid. In another embodiment, the acid is phosphoric acid. In yet another embodiment, the acid is hydrochloric acid.

The solution of the oxymorphone acid adduct formed corresponds with the acid utilised in the reaction. Thus oxymorphone acetate corresponds with acetic acid, oxymorphone phosphate with phosphoric acid, oxymorphone citrate with citric acid, oxymorphone tartrate with tartaric acid, oxymorphone oxalate with oxalic acid, oxymorphone hydrochloride with hydrochloric acid and oxymorphone hydrobromide with hydrobromic acid.

Any suitable wt/wt ratio of water:acid may be used. For example, the wt/wt ratio of water:acid may be from about 10:0.01 to about 0.01:10, such as about 3.0:1 to about 4.0:1, such as about 3.3:1 or 3.4:1.

The wt/wt ratio of 14-hydroxymorphinone:acid may be in the range of about 0.01:10 g/g to about 10:0.1 g/g, such as about 1:1 to about 1.5:1 g/g, for example 1.30:1 to about 1.35:1 g/g. The ratio of 14-hydroxymorphinone:water may be in the range of about to about 1:0.005 to about 1:10, such as about 1:0.01 to about 1:3.0 g/g, for example about 1:2.5 g/g. The quantities of water and/or acid are not particularly limiting provided there is enough water and/or acid to substantially dissolve the 14-hydroxymorphinone. The quantity of water present in the catalyst and/or 14-hydroxymorphinone (which may also be used wet) may be taken into account when calculating the total quantity of water to be used.

The 14-hydroxymorphinone is substantially dissolved in the water and acid. The dissolution of the 14-hydroxymorphinone may be encouraged through the use of an aid such as stirring and/or sonication.

Conventionally, the hydrogenation of 14-hydroxymorphinone is carried out at an ambient temperature i.e. a temperature of 30° C. or less. In the present process, however, the hydrogenation is carried out at one or more temperatures greater than 40° C. and below the boiling point of the reaction mixture. The boiling point of the reaction mixture may vary depending on the pressure under which the hydrogenation reaction is conducted. In one embodiment, the hydrogenation may be carried out at one or more temperatures in the range of ≥about 50° C. to about ≤about 100° C. In some embodiments, the hydrogenation is carried out at one or more temperatures ≥about 55° C. In some embodiments, the hydrogenation is carried out at one or more temperatures ≥about 56° C. In some embodiments, the hydrogenation is carried out at one or more temperatures ≥about 57° C. In some embodiments, the hydrogenation is carried out at one or more temperatures ≥about 58° C. In some embodiments, the hydrogenation is carried out at one or more temperatures ≥about 59° C. In some embodiments, the hydrogenation is carried out at one or more temperatures ≥about 60° C. In some embodiments, the hydrogenation is carried out at one or more temperatures ≤about 95° C. In some embodiments, the hydrogenation is carried out at one or more temperatures ≤about 90° C. In some embodiments, the hydrogenation is carried out at one or more temperatures ≤about 85° C. In one preferred embodiment, the hydrogenation is carried out at one or more temperatures in the range of ≥ about 50° C. to ≤about 85° C., such as ≥about 55° C. to ≤about 80° C.

Figure 1:
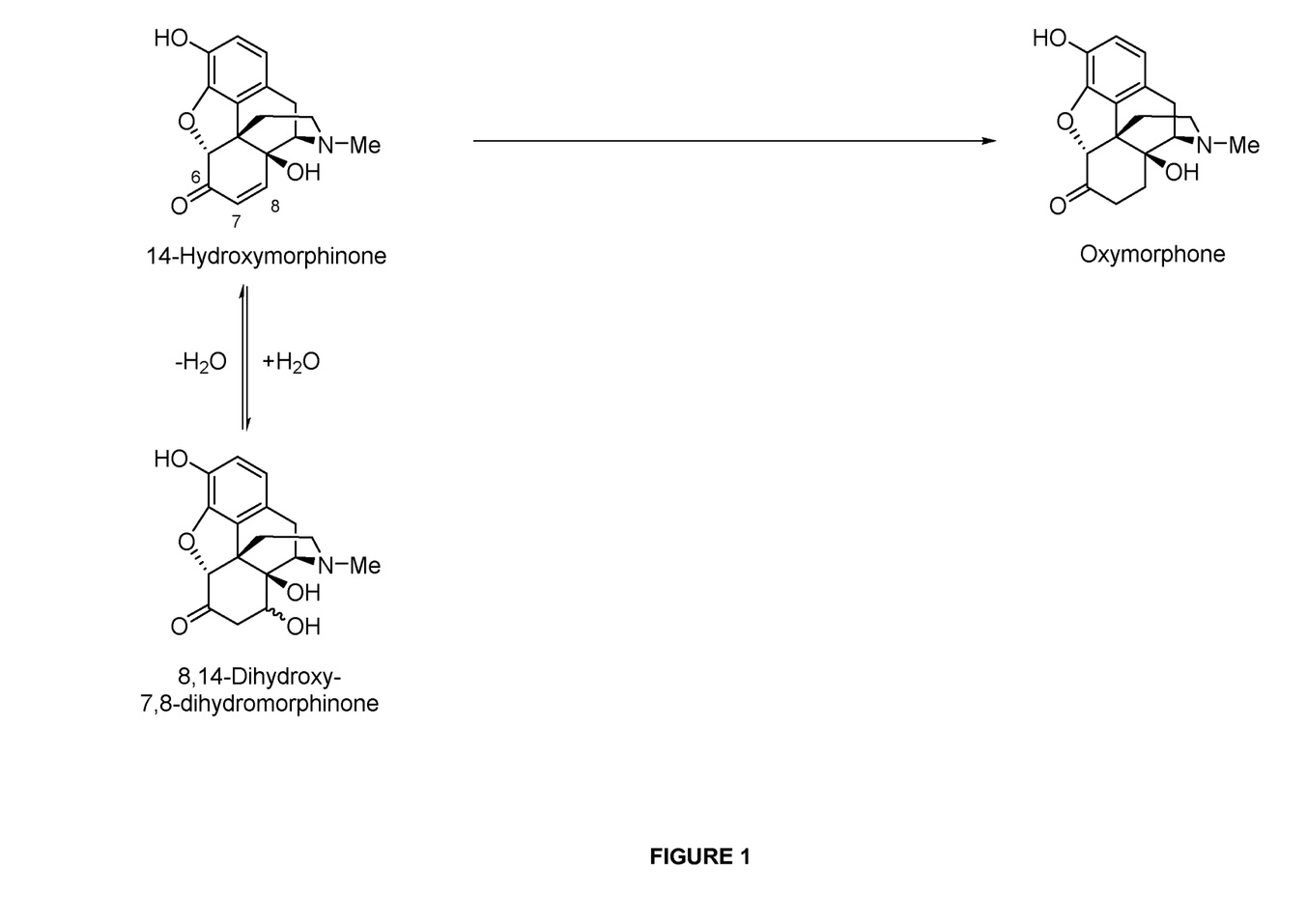
FIG. 1 illustrates a synthetic route for making oxymorphone.

The hydrogenation catalyst may be a heterogeneous or homogeneous catalyst, preferably a heterogeneous catalyst. The catalyst (whether heterogeneous or homogeneous) should be selected such that the catalyst preferentially reduces the double bond at C-7 and C-8 rather than reducing the C=O bond at C-6 (see FIG. 1). In one embodiment, the heterogeneous catalyst is a heterogeneous platinum group metal (PGM) catalyst, for example, a heterogeneous palladium or platinum catalyst. In one embodiment, the heterogeneous catalyst is a heterogeneous palladium catalyst. Examples of palladium catalysts include but are not limited to colloidal palladium, palladium sponge, palladium plate or palladium wire. Examples of platinum catalysts include but are not limited to colloidal platinum, platinum sponge, platinum plate or platinum wire.

The heterogeneous PGM metal catalyst may be a PGM on a solid support. The support may be selected from the group consisting of carbon, alumina, calcium carbonate, barium carbonate, barium sulfate, titania, silica, zirconia, ceria and a combination thereof. When the support is alumina, the alumina may be in the form of alpha-$Al_2O_3$, beta-$Al_2O_3$, gamma-$Al_2O_3$, delta-$Al_2O_3$, theta-$Al_2O_3$ or a combination thereof. When the support is carbon, the carbon may be in the form of activated carbon (e.g. neutral, basic or acidic activated carbon), carbon black or graphite (e.g. natural or synthetic graphite). An example of a heterogeneous PGM catalyst is palladium on carbon. An example of another heterogeneous PGM catalyst is platinum on carbon.

The catalyst loading may be up to about 20 mole %. In one embodiment, the catalyst loading may be up to 10 mole % and, in another embodiment, may be in the range of about 0.1-10.0 mole %.

While it is typically sufficient for a single charge of hydrogenation catalyst to be added to the reaction mixture, a second or further charge may be added and the hydrogenation continued if it has been determined (e.g. via in-process analysis) that the reaction has not gone to completion and starting material remains.

There is no particular limitation on the pressure at which the hydrogenation is carried out. In this regard, the hydrogenation may conveniently be carried out with an initial hydrogen pressure in the range of up to about 100 psi e.g. about 40±5 psi.

In carrying out the process of the invention at a temperature greater than 40° C., it is possible to obtain an oxymorphone acid adduct with an improved impurity profile. In one embodiment, it is possible to significantly reduce the levels of 6α-oxymorphol. While 6α-oxymorphol is not currently an impurity which is individually identified in an Official Monograph, such as the US Pharmacopeia, it is desirable to improve yields and reduce the number and quantities of impurities produced, particularly on an industrial scale. Typically, the oxymorphone hydrochloride ultimately prepared in a production campaign may have undergone several (or, indeed, many) processing treatments in order to reduce the level of 6α-oxymorphol, as well as other impurities, to sufficiently acceptable low levels. The processing treatments therefore can typically result in extended processing times on plant and loss in product yield. In carrying out the process of the present invention, however, the formation of 6α-oxymorphol can be minimised in the reaction which produces it as an impurity, thus reducing the requirement for further processing.

The present invention provides a process wherein the solution of oxymorphone acid adduct comprises 6α-oxymorphol in an amount ≤about 3.00 area % as determined by HPLC. In some embodiments, the solution of oxymorphone acid adduct comprises 6α-oxymorphol in an amount ≤about 2.50 area % as determined by HPLC. In some embodiments, the solution of oxymorphone acid adduct comprises 6α-oxymorphol in an amount ≤about 2.00 area % as determined by HPLC. In some embodiments, the solution of oxymorphone acid adduct comprises 6α-oxymorphol in an amount ≤about 1.50 area % as determined by HPLC. In some embodiments, the solution of oxymorphone acid adduct comprises 6α-oxymorphol in an amount ≤about 1.40 area % as determined by HPLC. In some embodiments, the solution of oxymorphone acid adduct comprises 6α-oxymorphol in an amount ≤about 1.30 area % as determined by HPLC. In some embodiments, the solution of oxymorphone acid adduct comprises 6α-oxymorphol in an amount ≤about 1.20 area % as determined by HPLC. In some embodiments, the solution of oxymorphone acid adduct comprises 6α-oxymorphol in an amount ≤about 1.10 area % as determined by HPLC. In some embodiments, the solution of oxymorphone acid adduct comprises 6α-oxymorphol in an amount ≤about 1.00 area % as determined by HPLC. In some embodiments, the solution of oxymorphone acid adduct comprises 6α-oxymorphol in an amount ≤about 0.90 area % as determined by HPLC. In some embodiments, the solution of oxymorphone acid adduct comprises 6α-oxymorphol in an amount ≤about 0.80 area % as determined by HPLC. In some embodiments, the solution of oxymorphone acid adduct comprises 6α-oxymorphol in an amount ≤about 0.700 area % as determined by HPLC. In some embodiments, the solution of oxymorphone acid adduct comprises 6α-oxymorphol in an amount ≤about 0.600 area % as determined by HPLC. A suitable HPLC method for determining the amount of 6α-oxymorphol is, for example, the HPLC method detailed below.

It has been found that in order to minimise the production of 6α-oxymorphol, the reaction mixture is generally heated to temperature before the hydrogenation reaction starts. Example 1 illustrates that when the hydrogenation is carried out at temperatures <40° C., the amount of 6α-oxymorphol in solution on reaction completion is high at 4.00 area %. In contrast, Examples 2 and 3 describe reactions according to the invention where 6α-oxymorphol is produced in the post-hydrogenation liquors in much lower quantities i.e. 0.6 area % and 1.10 area % respectively.

Heating the reaction mixture to temperature may be carried out after purging the reaction vessel with one or more nitrogen/vacuum cycles (e.g. one, two or three cycles). During purging the reaction mixture may be agitated to encourage removal of dissolved oxygen. After the final purge cycle the vessel may be left under vacuum and agitated (by either stirring or shaking) whilst the vessel is heated. Once the reaction mixture reaches the desired temperature, the hydrogenation reaction may begin by exposing the reaction mixture to hydrogen gas.

The hydrogenation reaction is carried out for a period of time until it is determined that the reaction is complete. Completion of the reaction may be determined by in-process analysis or by identifying that there is no longer an uptake of hydrogen gas. Typically the hydrogenation is complete within 1 or 2 hours, and in some embodiments, within 30 minutes. The reaction mixture, however, may be held at temperature and pressure for up to about 24 hours.

On completion of the reaction, the reaction vessel may be cooled and purged to remove excess hydrogen gas (or vice versa). The hydrogenation catalyst may be removed by any appropriate method, such as filtration, and the filtrate (containing the oxymorphone acid adduct) may be further treated as desired.

In one embodiment, the process further comprises treating the solution of oxymorphone acid adduct to form solid oxymorphone acid adduct. Examples of solid oxymorphone adducts include but are not limited to oxymorphone acetate or oxymorphone hydrochloride. If the hydrogenation is carried out in hydrochloric acid, solid oxymorphone hydrochloride may be isolated from the reaction mixture. It is also envisaged that the solution of oxymorphone acid adduct may undergo a salt exchange to form a solution of oxymorphone acid adduct comprising a different acid. For example, a solution of oxymorphone acetate may undergo a salt exchange to form a solution of oxymorphone hydrochloride.

In yet another embodiment, the process further comprises treating the solution of oxymorphone acid adduct with a base to form oxymorphone alkaloid. An example of a suitable base is ammonium hydroxide. Sufficient base is typically added so that the oxymorphone alkaloid precipitates out of solution.

Generally, oxymorphone alkaloid precipitate starts to become visible at about pH 7 and typically sufficient base is added to increase the pH to above 9. This ensures that the oxymorphone alkaloid is in free base form, as well as allowing maximum recovery of the oxymorphone alkaloid.

In another embodiment, the process further comprises treating the solid oxymorphone acid adduct to form oxymorphone alkaloid. This may be carried out by redissolving the solid oxymorphone acid adduct to form a solution of oxymorphone acid adduct and treating the solution with a base as described above. The oxymorphone alkaloid may be collected (e.g. by filtration), optionally washed one or more times and dried.

In some embodiments, the oxymorphone alkaloid comprises 6α-oxymorphol in an amount ≤about 1.30 area % as determined by HPLC. In some embodiments, the oxymorphone alkaloid comprises 6α-oxymorphol in an amount ≤about 1.20 area % as determined by HPLC. In some embodiments, the oxymorphone alkaloid comprises 6α-oxymorphol in an amount ≤about 1.10 area % as determined by HPLC. In some embodiments, the oxymorphone alkaloid comprises 6α-oxymorphol in an amount ≤about 1.00 area % as determined by HPLC. In some embodiments, the oxymorphone alkaloid comprises 6α-oxymorphol in an amount ≤about 0.90 area % as determined by HPLC. In some embodiments, the oxymorphone alkaloid comprises 6α-oxymorphol in an amount ≤about 0.80 area % as determined by HPLC. In some embodiments, the oxymorphone alkaloid comprises 6α-oxymorphol in an amount ≤about 0.70 area % as determined by HPLC. In some embodiments, the oxymorphone alkaloid comprises 6α-oxymorphol in an amount ≤about 0.60 area % as determined by HPLC. A suitable HPLC method for determining the amount of 6α-oxymorphol is provided below.

In yet another embodiment, the oxymorphone alkaloid may be slurried with a liquid alcohol and heated with stirring. On cooling with further stirring, the oxymorphone alkaloid may be collected (e.g. by filtration), optionally washed one or more times with an alcohol and dried. The alcohol may be a straight-chain, branched or cyclic $C_{1-10}$-alkanol and may be selected from the group consisting of methanol, ethanol, propanols (n- or i-), butanols (n-, i- or t-), pentanols, hexanols and heptanols. In one embodiment, the alcohol may be n-propanol. The inventors have found that treatment of the oxymorphone alkaloid in this way further reduces the level of 6α-oxymorphol. In some embodiments, therefore, the oxymorphone alkaloid isolated comprises 6α-oxymorphol in an amount ≤about 0.20 area % as determined by HPLC. In some embodiments, the oxymorphone alkaloid isolated comprises 6α-oxymorphol in an amount ≤about 0.15 area % as determined by HPLC. In some embodiments, the oxymorphone alkaloid isolated comprises 6α-oxymorphol in an amount ≤about 0.10 area % as determined by HPLC.

Treatment of the oxymorphone alkaloid with the liquid alcohol also reduces the level of 6β-oxymorphol. In some embodiments, the oxymorphone alkaloid isolated comprises 6β-oxymorphol in an amount ≤about 0.200 area % as determined by HPLC. In some embodiments, the oxymorphone alkaloid comprises 6β-oxymorphol in an amount ≤about 0.175 area % as determined by HPLC. In some embodiments, the oxymorphone alkaloid comprises 6β-oxymorphol in an amount ≤about 0.150 area % as determined by HPLC. In some embodiments, the oxymorphone alkaloid comprises 6β-oxymorphol in an amount ≤about 0.100 area % as determined by HPLC. In some embodiments, the oxymorphone alkaloid comprises 6β-oxymorphol in an amount undetectable by HPLC.

Other impurities which may be present oxymorphone alkaloid and acid adducts thereof include α,β-unsaturated ketones (ABUKs), such as 14-hydroxymorphinone or morphinone. There has been much recent concern over ABUKs due to their proposed biological activities as genotoxins. As such, there is a continuing need to develop processes which produce low ABUK oxymorphone alkaloid and low ABUK oxymorphone salts, such as low ABUK oxymorphone hydrochloride. Without wishing to be bound by theory, it appears that the 14-hydroxymorphinone which may be present as an impurity in oxymorphone alkaloid or acid adduct thereof originates from two sources—firstly, residual unreacted 14-hydroxymorphinone starting material and secondly, indirectly from 8,14-dihydroxy-7,8-dihydromorphinone which, it has been argued, converts to 14-hydroxymorphinone under acidic conditions (see FIG. 1). Thus, even if the reactions conditions are capable of driving a reaction to form oxymorphone having <10 ppm of 14-hydroxymorphinone, the ABUK, 14-hydroxymorphinone, may be generated during salt formation via the dehydration of 8,14-dihydroxy-7,8-dihydromorphinone. In this regard, 8,14-dihydroxy-7,8-dihydromorphinone may be present in the hydrogenation of 14-hydroxymorphinone to oxymorphone as it may be present as an impurity in the 14-hydroxymorphinone starting material. It may, therefore, be carried forward in the transformation of 14-hydroxymorphinone to oxymorphone, as well as subsequent salt formation to form an oxymorphone salt. Likewise, the ABUK morphinone may be generated during salt formation via the dehydration of the precursor 8-hydroxy-7,8-dihydromorphinone (not shown in FIG. 1).

In one embodiment, therefore, the oxymorphone acid adduct or oxymorphone alkaloid prepared according to the present invention comprises ≤about 50 ppm of an α,β-unsaturated ketone, such as about 25 ppm of an α,β-unsaturated ketone, for example, ≤about 15 ppm of an α,β-unsaturated ketone. In one preferred embodiment, the oxymorphone acid adduct or alkaloid comprises ≤about 10 ppm of an α,β-unsaturated ketone. In another embodiment, the oxymorphone acid adduct or alkaloid is substantially free of an α,β-unsaturated ketone. The α,β-unsaturated ketone may be selected from the group consisting of 14-hydroxymorphinone, morphinone and a mixture thereof. Without wishing to be bound by theory, it is believed that the temperature at which the present invention is carried out (i.e. greater than 40° C.) is capable of simultaneously dehydrating 8,14-dihydroxy-7,8-dihydromorphinone (to produce 14-hydroxymorphinone), hydrogenating 14-hydroxymorphinone (to form oxymorphone), dehydrating 8-hydroxy-7,8-dihydromorphinone, if present (to form morphinone) and hydrogenating morphinone, if present (to form hydromorphone).

In another aspect, the invention provides process for preparing an oxymorphone acid adduct, said process comprising hydrogenating an aqueous solution of 14-hydroxymorphinone and an acid to form a solution of the oxymorphone acid adduct, wherein the hydrogenation is carried out at one or more temperatures greater than ambient temperature in the presence of a hydrogenation catalyst and hydrogen gas, wherein the solution of oxymorphone acid adduct comprises less 6α-oxymorphol than that produced on carrying out the hydrogenation at 40° C. or less.

All of the embodiments described above, such as the hydrogenation conditions, the hydrogenation catalyst and the minimisation in the level of 6α-oxymorphol produced generally likewise apply to this aspect of the invention.

In another aspect, the present invention provides a process for preparing an oxymorphone acid adduct, said process comprising hydrogenating 14-hydroxymorphinone and an acid in a solvent comprising an alcohol and optionally water to form the oxymorphone acid adduct, wherein the hydrogenation is carried out at one or more temperatures greater than ambient temperature in the presence of a hydrogenation catalyst and hydrogen gas, wherein the oxymorphone acid adduct comprises less 6α-oxymorphol than that produced on carrying out the hydrogenation at 40° C. or less.

All of the embodiments described above, such as the hydrogenation conditions, the hydrogenation catalyst and the minimisation in the level of 6α-oxymorphol, produced generally likewise apply to this aspect of the invention.

The solvent comprises an alcohol and optionally water. The alcohol may be a straight-chain, branched or cyclic $C_{1-10}$-alkanol and may be selected from the group consisting of methanol, ethanol, propanols (n- or i-), butanols (n-, i- or t-), pentanols, hexanols and heptanols. In one embodiment, the alcohol may be ethanol.

As mentioned above, the hydrogenation is carried out at one or more temperatures greater than 40° C. and below the boiling point of the reaction mixture. The skilled person would understand and take into account that the pressure of the reaction and the effect that it may have on the boiling point of the reaction mixture.

In yet another aspect, the present invention provides an aqueous solution of oxymorphone acid adduct comprising 6α-oxymorphol in an amount ≤about 3.00 area % as determined by HPLC. In one embodiment, the oxymorphone acid adduct is oxymorphone acetate or oxymorphone hydrochloride. In another embodiment, the aqueous solution of oxymorphone acid adduct further comprises ≤about 50 ppm of an α,β-unsaturated ketone, ≤ preferably ≤about 25 ppm.

In another aspect, the present invention provides solid oxymorphone acid adduct comprising 6α-morphol in an amount ≤about 3.00 area % as determined by HPLC, preferably ≤about 1.10 area %. In one embodiment, the oxymorphone acid adduct is oxymorphone acetate or oxymorphone hydrochloride. In another embodiment, the solid oxymorphone acid adduct further comprises ≤about 50 ppm of an α,β-unsaturated ketone, preferably ≤about 25 ppm.

In yet another aspect, the present invention provides solid oxymorphone alkaloid comprising 6α-oxymorphol in an amount ≤about 1.30 area % as determined by HPLC, preferably ≤about 0.60 area %. In one embodiment, the oxymorphone alkaloid further comprises ≤about 50 ppm of an α,β-unsaturated ketone, preferably ≤about 25 ppm.

Embodiments and/or optional features of the invention have been described above. Any aspect of the invention may be combined with any other aspect of the invention, unless the context demands otherwise. Any of the embodiments or optional features of any aspect may be combined, singly or in combination, with any aspect of the invention, unless the context demands otherwise.

The invention will now be described by way of the following non-limiting Examples.

EXAMPLES

General

HPLC Method
1.1 Reagents/Materials/Instrumentation:

| Reagent/Material | Supplier, Grade |
|---|---|
| Water ($H_2O$) | Waters Milli Q System, 18 MOhm |
| Acetonitrile (ACN) | Fisher Optima |
| Methanol (MeOH) | Fisher Optima |
| Ammonium Phosphate dibasic [$(NH_4)_2HPO_4$] | EMD Chemicals, ACS Grade |
| O-Phosphoric Acid ($H_3PO_4$) | EMD Chemicals, HPLC Grade, 85% |
| Oxymorphone HCl | JM Qualified Reference Standard |
| 6α-Oxymorphol | JM Qualified Reference Standard |
| Pseudo-oxymorphone | Authentic Material (as Retention Time marker) |
| Oxymorphone-N-oxide | Authentic Material (as Retention Time marker) |
| Retention Time Marker solution | Pre-vialed JM solution |

| Instrument | Description |
|---|---|
| Detector | Waters, 2487 UV/VIS Detector |
| Chromatograph | Waters, 2690 Separations Module |
| Data System | Chromatography Data System, current JM version |
| Balance | Mettler-Toledo, Model AT261 or PG503-S, Delta Range |

1.2 Operating Conditions:

| Conditions | Description |
|---|---|
| Column | Phenomenex Gemini $C_{18}$ 3 µm 150 mm × 3.0 mm |
| Injection Volume | 7 µL |
| Column Temperature | 40° C. |
| Sample Temperature | 15° C. |
| Detection | UV @ 212 nm |
| Flow Rate | 0.6 mL/min |
| Analysis Time | 24 minutes |
| Run Time | 30 minutes |

| | Time (min) | % MP A | % MP B | Curve |
|---|---|---|---|---|
| Gradient Profile: | Initial | 99 | 1 | 6 |
| | 20 | 1 | 99 | 6 |
| | 24 | 1 | 99 | 6 |
| | 24.1 | 99 | 1 | 6 |
| | 30 | 99 | 1 | 6 |
| Seal Wash | 80% $H_2O$ | 10% MeOH | 10% ACN | Degassed |
| Needle Wash | Equal volumes of $H_2O$, MeOH, ACN | | | Degassed |
| Column Wash | 80% $H_2O$ | 20% MeOH | | Degassed |

1.3 Approximate Retention Times of Known Analytes:

| Analyte | Approximate RT (min) | RRT |
|---|---|---|
| Oxymorphone-N-oxide | 4.5 | 0.45 |
| 6α-Oxymorphol | 9.0 | 0.90 |
| Oxymorphone | 10.0 | 1.00 |
| 14-Hydroxymorphinone | 11.0 | 1.10 |
| Pseudo-oxymorphone | 15.0 | 1.50 |

1.4 Mobile Phase Preparation:
Mobile Phase A:
  Into a suitable container, transfer 1.4 g of $(NH_4)_2HPO_4$.
  Transfer 900-mL of $H_2O$ into the container and mix well to dissolve the salt.
  Transfer 70-mL of MeOH and 30-mL of ACN into the container and mix the solution well.
  Filter and degas the solution.
Mobile Phase B:
  Into a suitable container, transfer 1.2 g of $(NH_4)_2HPO_4$.
  Transfer 400-mL of $H_2O$ into the container and mix well to dissolve the salt.
  Transfer 450-mL of MeOH and 150-mL of ACN into the container and mix the solution well.

Filter and degas the solution.

Note: This will produce about 1 L of each mobile phase. If more/less is required, adjust the volumes accordingly for each component.

1.5 Diluent Preparation:

Transfer 900-mL of $H_2O$ into a suitable container.

Transfer 30-mL of ACN and 70-mL of MeOH into the container.

Transfer 0.5-mL $H_3PO_4$ into the container and mix the solution well.

Note: This will produce about 1 L of diluent. If more/less is required, adjust the volumes accordingly for each component.

1.6 Reference Standard Preparation:

Impurity Standard Solution:

Accurately weigh approximately 25-mg of 6α-Oxymorphol, 5-mg each of Pseudo-oxymorphone and Oxymorphone-N-oxide and transfer into a 100-mL volumetric flask.

Transfer approximately 50-mL of diluent into the flask and dissolve with mixing and sonication.

Dilute the solution to volume with diluent and mix the solution well. (Stock solution A).

Transfer 1.0-mL of the Stock Solution "A" into the 50-mL volumetric flask, add about 25-mL of diluent and dissolve with mixing and sonication.

Dilute to volume with diluent and mix the solution well. (Impurity Standard Solution).

The concentration is approximately 0.005 mg/mL for 6α-Oxymorphol, 0.001 mg/mL each of Oxymorphone-N-oxide and Pseudo-oxymorphone (~0.5% w/w for 6α-Oxymorphol and ~0.10% area for Oxymorphone-N-oxide and Pseudo-oxymorphone each).

Retention Time Marker Solution:

Transfer 1.0-mL of the Stock Solution "A" into the 50-mL volumetric flask containing 50 mg Oxymorphone HCl, add about 25-mL of diluent and dissolve with mixing and sonication.

Dilute to volume with diluent and mix the solution well. (Resolution Solution).

The concentration is approximately 0.005 mg/mL for 6α-Oxymorphol, 0.001 mg/mL each of Oxymorphone-N-oxide and Pseudo-oxymorphone and 1.0 mg/mL of Oxymorphone HCl (~0.5% w/w for 6α-Oxymorphol and 0.10% area for Oxymorphone-N-oxide and Pseudo-oxymorphone each). This solution can be pre-vialed and stored in a freezer for future use.

1.7 Sample Solution Preparation:

In duplicate, accurately weigh approximately 50-mg of Oxymorphone sample and transfer into a 50-mL volumetric flask.

Transfer approximately 40-mL of diluent into the flask and dissolve the sample (mixing and sonication).

Dilute the solution to volume with diluent and mix well.

The concentration is approximately 1.0 mg/mL for Oxymorphone.

1.8 System Equilibration:

Pump mobile phase B at method conditions for 15 minutes and until a stable baseline is obtained.

Pump the initial method conditions until a stable baseline is obtained.

Inject 50-μL of the diluent and run the gradient profile through the system.

1.9 Procedure:

Inject the diluent.

Inject the Retention Time Marker Solution once.

Inject the Impurity Standard Solution 6 times.

Ensure all system suitability requirements are met.

Inject each sample solution in duplicate.

Inject the Impurity Standard Solution 2 times as a standard check.

Note: To maintain the column, mobile phase lines must be washed with 80:20 Water:Methanol and the column temperature lowered to ambient at the end of the run.

1.10 System Suitability:

Note: Make the necessary chromatographic adjustment(s) to achieve the system suitability requirement(s).

USP Tailing:

The tailing factor of the Oxymorphone peak in the Retention Time Marker injection must be NMT 1.5. Refer to current USP calculation.

Precision:

The % RSD of the average peak area response from six injections of the Impurity Standard solution must be NMT 10.0 for 6α-Oxymorphol.

USP Resolution:

The resolution between the 6α-Oxymorphol, Pseudo-oxymorphone, Oxymorphone-N-oxide and Oxymorphone peaks in the Retention Time Marker solution must be NLT 1.2. Refer to current USP calculation.

Standard Check:

A % difference between the averaged peak area of the six Impurity Standard solution injections for precision and the averaged peak area of the two standard check injections must be NMT 25.0 for 6α-Oxymorphol.

1.11 Calculations:

$$\% \ w/w \ 6\text{-}\alpha\text{-Oxymorphol} = \frac{Smp^{AvgPA} \times 100 \times Std^{Conc} \times \text{Purity(decimal)}}{Std^{AvgPA} \times Smp^{Conc}}$$

$$\% \ \text{Area Unspecified Impurity} = \frac{Imp^{AvgPA} \times 100}{\text{Total } PA \text{ in chromatogram}}$$

Total Impurities=Σ% Specified Impurities+Σ% Unspecified Impurities

Where:

PA=Peak Area Std=Standard Smp=Sample

Imp=Impurity Conc=Concentration, mg/mL

Chromatography Data System Calculations:

$$Std=Std \ (mg/mL) \times \text{Purity(decimal)} \times 100$$

$$\text{Sample}=Smp \ (mg/mL)$$

1.12 Typical Chromatograms

Figure 2:
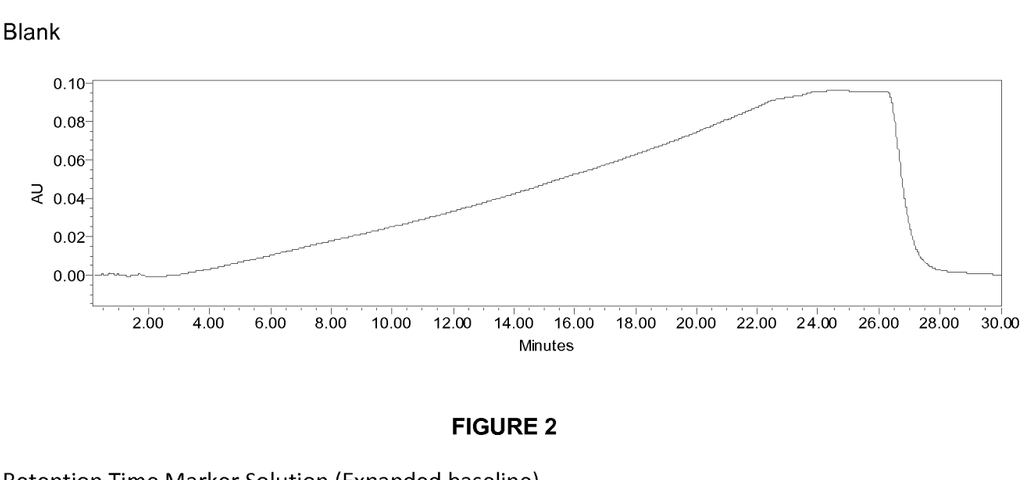
FIG. 2 illustrates a typical chromatogram of the diluent as a blank.

FIG. 2 shows a typical chromatogram of the diluent as blank.

Figure 3:
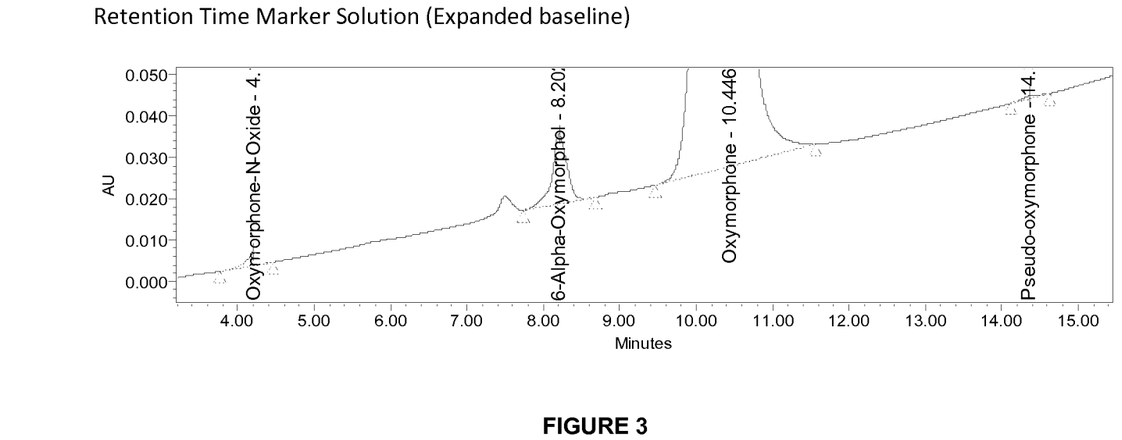
FIG. 3 illustrates a typical chromatogram of the Retention Time Marker Solution (expanded baseline).

FIG. 3 shows a typical chromatogram of the Retention Time Marker Solution (expanded baseline).

Figure 4:
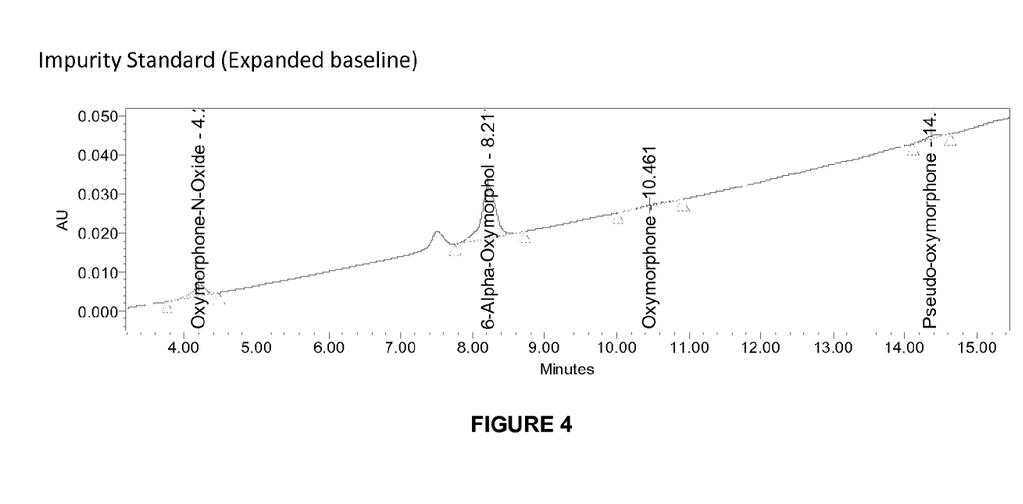
FIG. 4 illustrates a typical chromatogram of the Impurity Standard (expanded baseline).
Figure 5:
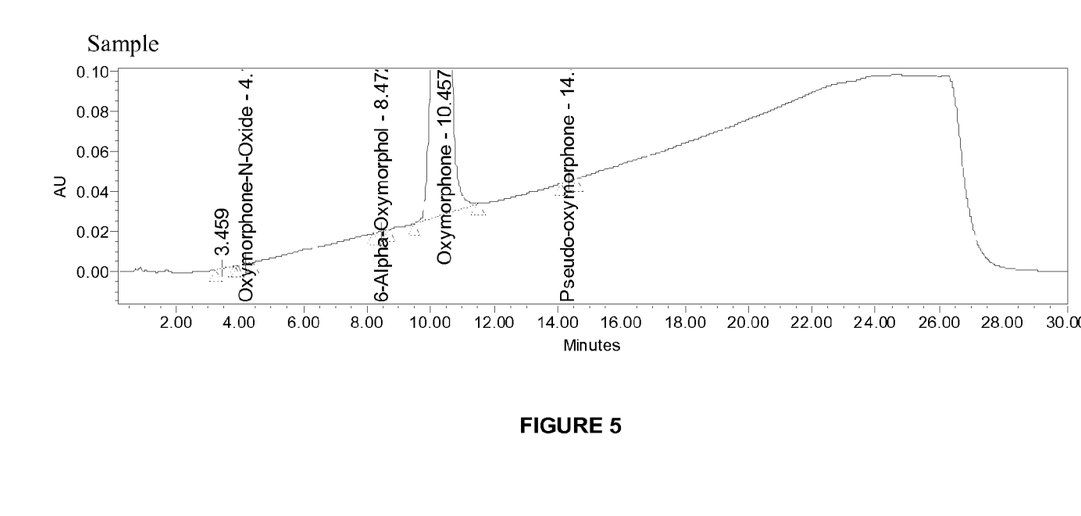
FIG. 5 illustrates a typical chromatogram of a sample in accordance with an embodiment of the invention.

FIG. 4 shows a typical chromatogram of the Impurity Standard (expanded baseline).
FIG. 5 shows a typical chromatogram of a Sample.

Example 1

Comparative 14-hydroxymorphinone

1. Pd/C, water/acetic acid,
2. hydrogenate at 40 psi, 30 ± 5° C.
3. Aq NH₄OH to pH 9.0-9.5
4. 1-Propanol Slurry
5. filter and dry at 50° C.

Oxymorphone

To a stainless steel pressure vessel was charged water (150 g), acetic acid (44 g) and 14-hydroxymorphinone (60 g dry). The mixture was stirred under N₂ until all solids dissolved. To this solution was charged 5% Pd/C (57.8% wet, 2.4 g dry weight). The vessel was sealed and evacuated and purged with N₂ three times. Under a slight vacuum, the vessel was heated to 30±5° C. and H₂ was charged to 35-40 psi. A slight temperature exotherm was observed over 20 minutes as the temperature increased to 39° C. After 20 minutes the H₂ uptake stopped and the reaction was held at 35-40 psi and 30±5° C. for an additional 2 h.

A sample was pulled from the reaction and HPLC analysis indicated no detectable 14-hydroxymorphinone remained. The 6α-oxymorphol was determined to be 4.0 area %. The batch was warmed to 45±5° C. and filtered through 20 g of Celite. The filtrate was then passed through a 0.45µ membrane filter.

The filtrate was cooled to <16° C. and adjusted to pH 9.35 keeping the temperature 9-16° C. with the addition of a 1:1 wt/wt mixture of NH₄OH/water (~104 g total used). The slurry was stirred at room temperature for 1 h and the pH 9.15 slurry was filtered to collect the solids. The filter cake was washed with water (2×120 g) and dried on the filter 10 min. to give 64.2 g wet product as a tan solid (LOD analysis was 17.8%).

The wet solid was transferred to a reaction vessel and suspended in 1-propanol (144.6 g) and heated to 92±2° C. for 1 h. The solution was then slowly cooled to room temperature and stirred 3 h. Filtration at room temperature gave Oxymorphone Base (40.4 g, 66.9% yield) as an off-white solid.

HPLC Analysis

HPLC data for the crude Oxymorphone Base prior to and after 1-propanol slurry purification.

|  | 6α-Oxymorphol (before 1-propanol slurrying) (% w/w) | | 6α-Oxymorphol (after 1-propanol slurrying) (% w/w) | |
| --- | --- | --- | --- | --- |
|  | Run 1 | Run 2 | Run 1 | Run 2 |
| Oxymorphone base | 1.34 | 1.38 | 0.22 | 0.22 |

Example 2

According to the Invention 14-hydroxymorphinone

1. Pd/C, water/acetic acid,
2. hydrogenate at 40 psi, 70 ± 10° C.
3. Aq NH₄OH to pH 9.0-9.5
4. 1-Propanol Slurry
5. filter and dry at 50° C.

Oxymorphone

To a stainless steel pressure vessel was charged water (75 g), acetic acid (22 g) and 14-hydroxymorphinone (30 g dry). The mixture was stirred under N₂ until all solids dissolved. To this solution was charged 5% Pd/C (57.8% wet, 1.2 g dry weight). The vessel was sealed and evacuated and purged with N₂ three times. Under a slight vacuum, the vessel was heated to 60±5° C. and H₂ was charged to 35-40 psi. A slight temperature exotherm was observed over 20 minutes as the temperature increased to 69° C. After 1 h the H₂ uptake stopped and the reaction was held at 35-40 psi and 70±10° C. for an additional 20 h.

A sample was pulled from the reaction and HPLC analysis indicated 14-hydroxymorphinone <0.2 area %. The 6α-oxymorphol was determined to be 0.6 area %. The batch was cooled to 45±5° C. and filtered through 7 g of Celite, washing with water (2×30 g). The filtrate was then passed through a 0.45µ membrane filter.

The filtrate was cooled to 10° C. and adjusted to pH 9.35 keeping the temperature 9-16° C. with the addition of a 1:1 wt/wt mixture of NH₄OH/water. The slurry was stirred at room temperature for 1.5 h and the pH 9.15 slurry was filtered to collect the solids. The filter cake was washed with water (2×60 g) and dried on the filter 10 min. to give 36.0 g as a wet solid (LOD analysis was 18.6%).

The wet solid was transferred to a reaction vessel and suspended in 1-propanol (36.0 g) and heated to 92±2° C. for 1.25 h. The solution was then slowly cooled to room temperature and stirred 2 h. Filtration at room temperature gave Oxymorphone Base (22.5 g, 74.5% yield) as an off-white solid.

HPLC Analysis

HPLC data for the crude Oxymorphone Base prior to and after 1-propanol slurry purification.

| | 6α-Oxymorphol (before 1-propanol slurrying) (% w/w) | | 6α-Oxymorphol (after 1-propanol slurrying) (% w/w) | |
|---|---|---|---|---|
| | Run 1 | Run 2 | Run 1 | Run 2 |
| Oxymorphone base | 0.30 | 0.31 | 0.09 | 0.09 |

Example 3

According to the Invention 14-hydroxymorphinone

1. Pd/C, water/acetic acid,
2. hydrogenate at 40 psi, 70 ± 10° C.
3. Aq NH$_4$OH to pH 9.0-9.5
4. 1-Propanol Slurry
5. filter and dry at 50° C.

Oxymorphone

To a stainless steel pressure vessel was charged water (500 g), acetic acid (150 g) and 14-hydroxymorphinone (200 g dry basis). The mixture was stirred under N$_2$ until all solids dissolved. To this solution was charged 5% Pd/C (4.4% wet, 8.0 g dry weight). The vessel was sealed and evacuated and purged with N$_2$ three times. Under a slight vacuum, the vessel was heated to 60.0° C. and hydrogen was charged to 39 psi. A slight temperature exotherm was observed over 10 minutes as the temperature increased to 62° C. After 20 minutes the temperature was adjusted to 70° C. After 1 h since the charge of H$_2$, the agitation was increased and the H$_2$ uptake increased for 10 minutes and then uptake stopped. During this time the reaction exotherm increased the temperature to 76° C. The pressure and temperature was maintained at 40 psi and 73-76° C. for 18.5 h.

The reaction mixture was cooled to 45±5° C., evacuated and purged with N$_2$ three times. The mixture was analyzed by HPLC and found to be complete (<0.1% 14-hydroxymorphinone remaining). The 6α-oxymorphol was determined to be 1.1 area %. A filter bed of Celite (10.0 g) was prepared on top of a 0.45 μmembrane filter. The bed was pre-washed and packed with water. The 45±5° C. reaction mixture was filtered through the Celite and membrane filter and the filtrate transferred to a 3000 mL reaction vessel. The pressure vessel was rinsed with water (2×200 g) and the rinse transferred to the filter to wash the Celite bed. The wash filtrate was transferred to the vessel containing the batch filtrate and the internal temperature was adjusted to 12.0° C.

A solution of NH$_4$OH and water (1:1 wt/wt, 308.2 g) was slowly added to the filtrate adjusting to pH 9.25 while keeping the temperature <20° C. The slurry mixture was stirred at 20° C. for 1.5 h and found to be pH 9.07. The product was collected by filtration washing with water (2×400 mL). The solid was dried on the filter for 0.5 h. LOD analysis (32.7%) indicated a crude Oxymorphone Base yield of 90.2% (181.5 g on dry basis, 99.0 area %, 6α-oxymorphol 0.52 area %, 6β-oxymorphol 0.20 area %).

The crude Oxymorphone Base (267.7 g wet, 180.1 g dry basis) was transferred back to a clean 3000 mL reaction vessel and 1-propanol (321.6 g) was charged. The slurry was heated to 90±3° C. and stirred for 1.5 h. The temperature was lowered to 25±5° C. and stirred for 1 h. The batch was further cooled to 10±5° C. and stirred 1 h. The product was collected by filtration washing the cake with 1-propanol (10±5° C., 2×48.2 g) then drying under vacuum at 55±5° C. to give Oxymorphone Base (167.8 g, 83.3% yield, 99.9 area %, 6α-oxymorphol 0.11 area %, 6β-oxymorphol not detected).

The invention claimed is:

1. A process for preparing an oxymorphone acid adduct, said process comprising hydrogenating an aqueous solution of 14-hydroxymorphinone and an acid to form a solution of the oxymorphone acid adduct, wherein the hydrogenation is carried out at one or more temperatures greater than 40° C. in the presence of a hydrogenation catalyst and hydrogen gas, wherein the aqueous solution is heated to temperature before being exposed to the hydrogen gas, and wherein the solution of oxymorphone acid adduct comprises 6α-oxymorphol in an amount ≤3.00 area % as determined by HPLC.

2. A process according to claim 1, wherein the acid is selected from the group consisting of acetic acid, phosphoric acid, citric acid, tartaric acid, oxalic acid, hydrochloric acid, hydrobromic acid and a mixture thereof.

3. A process according to claim 1, wherein the hydrogenation is carried out at one or more temperatures in the range of about ≥50° C. to about ≤100° C.

4. A process according to claim 3, wherein the hydrogenation is carried out at one or more temperatures in the range of ≥about 50° C. to about ≤85° C.

5. A process according to claim 1, wherein the hydrogenation catalyst is a heterogeneous or homogenous catalyst, preferably a heterogeneous catalyst.

6. A process according to claim 5, wherein the heterogeneous catalyst is a heterogeneous platinum group metal (PGM) catalyst, preferably a heterogeneous palladium catalyst.

7. A process according to claim 1, wherein the solution of oxymorphone acid adduct comprises 6α-oxymorphol in an amount ≤about 1.10 area % as determined by HPLC.

8. A process according to claim 1, wherein the process further comprises treating the solution of oxymorphone acid adduct to form solid oxymorphone acid adduct.

9. A process according to claim 8, wherein the process further comprises treating the solid oxymorphone acid adduct to form oxymorphone alkaloid.

10. A process according to claim 1, wherein the process further comprises treating the solution of oxymorphone acid adduct with a base to form oxymorphone alkaloid.

11. A process according to claim 9, wherein the oxymorphone alkaloid comprises 6α-oxymorphol in an amount ≤about 1.10 area % as determined by HPLC.

12. A process according to claim 10, wherein the oxymorphone alkaloid comprises 6α-oxymorphol in an amount ≤about 1.10 area % as determined by HPLC.

13. A process according to claim 9, wherein the oxymorphone alkaloid comprises ≤about 50 ppm of an α,β-unsaturated ketone.

14. A process according to claim 10, wherein the oxymorphone alkaloid comprises ≤about 50 ppm of an α,β-unsaturated ketone.

15. A process according to claim 11, wherein the oxymorphone alkaloid comprises ≤about 50 ppm of an α,β-unsaturated ketone.

16. A process according to claim 12, wherein the oxymorphone alkaloid comprises ≤about 50 ppm of an α,β-unsaturated ketone.

17. A process according to claim 1, wherein the oxymorphone acid adduct comprises ≤about 50 ppm of an α,β-unsaturated ketone.

18. A process according to claim 8, wherein the oxymorphone acid adduct comprises ≤about 50 ppm of an α,β-unsaturated ketone.

19. A process for preparing an oxymorphone acid adduct, said process comprising hydrogenating an aqueous solution of 14-hydroxymorphinone and an acid to form a solution of the oxymorphone acid adduct, wherein the hydrogenation is carried out at one or more temperatures greater than 40° C. in the presence of a hydrogenation catalyst and hydrogen gas, wherein the aqueous solution is heated to temperature before being exposed to the hydrogen gas, and wherein the solution of the oxymorphone acid adduct comprises less 6α-oxymorphol than that produced on carrying out the hydrogenation at 40° C. or less.

20. A process for preparing an oxymorphone acid adduct, said process comprising hydrogenating 14-hydroxymorphinone and an acid in a solvent comprising an alcohol and optionally water to form the oxymorphone acid adduct, wherein the hydrogenation is carried out at one or more temperatures greater than ambient temperature in the presence of a hydrogenation catalyst and hydrogen gas, wherein the 14-hydroxymorphinone, acid and solvent are heated to temperature before being exposed to the hydrogen gas, and wherein the oxymorphone acid adduct comprises less 6α-oxymorphol than that produced on carrying out the hydrogenation at ambient temperature.

\* \* \* \* \*